US010458976B2

United States Patent
Deshpande et al.

(10) Patent No.: US 10,458,976 B2
(45) Date of Patent: Oct. 29, 2019

(54) EARLY WARNING OF CHANGES IN HEALTH AND ROBUSTNESS USING NARROWLY FORWARD SCATTERED LIGHT TO TRACK EASE OF MORPHOLOGICAL CHANGES OF BLOOD CELLS

(71) Applicant: Satish Deshpande, Guelph (CA)

(72) Inventors: Satish Deshpande, Guelph (CA); James Andrew Estill, Guelph (CA); Donald Franklin Moyer, Chicago, IL (US)

(73) Assignee: Satish DESHPANDE, Guelph, ON (CA)

( * ) Notice: Subject to any disclaimer, the term of this patent is extended or adjusted under 35 U.S.C. 154(b) by 252 days.

(21) Appl. No.: 15/278,732

(22) Filed: Sep. 28, 2016

(65) Prior Publication Data
US 2017/0016882 A1   Jan. 19, 2017

Related U.S. Application Data

(63) Continuation-in-part of application No. 14/248,285, filed on Apr. 8, 2014, now abandoned.

(51) Int. Cl.
*G01N 33/96* (2006.01)
*G01N 33/49* (2006.01)
(Continued)

(52) U.S. Cl.
CPC ......... *G01N 33/5026* (2013.01); *G01N 21/51* (2013.01); *G01N 33/5044* (2013.01); *G01N 33/5091* (2013.01); *G01N 33/5094* (2013.01); *G01N 15/0211* (2013.01); *G01N 2015/0065* (2013.01); *G01N 2015/1006* (2013.01); *G01N 2015/1495* (2013.01);
(Continued)

(58) Field of Classification Search
CPC .......... G01N 21/51; G01N 2021/4707; G01N 33/5008; G01N 15/1456; G01N 2015/0065; G01N 2015/1488; G01N 2021/4711; G01N 2021/4723; G01N 21/274; G01N 33/502; G01N 33/5094; G01N 15/0211; G01N 15/14; G01N 2015/1006; G01N 2015/1495; G01N 2015/1497; G01N 33/00; G01N 33/48; G01N 33/5026; G01N 33/5044; G01N 33/5091; G06T 2207/30024; G06T 7/0012
USPC ........ 422/73; 436/10; 356/337, 39; 435/2, 3, 435/4, 5, 440
See application file for complete search history.

(56) References Cited

U.S. PATENT DOCUMENTS 5,445,939 A    8/1995   Anderson

OTHER PUBLICATIONS

Introduction to Flow Cytometry, LIT.FLOW, M. Rahman, Mar. 2006 (Year: 2006).*

(Continued)

*Primary Examiner* — Dean Kwak
(74) *Attorney, Agent, or Firm* — Gowling WLF (Canada); Jeffrey W. Wong (57) ABSTRACT

Early warning of changing health and robustness is given by tracking of ease of morphological changes in blood cells obtained by comparing intensities in a first scattered light intensity angular distribution and intensities in a second scattered light intensity angular distribution, with the light being scattered by blood cells into very narrowly forward scattered light intensity angular range.

8 Claims, 7 Drawing Sheets

(51) Int. Cl.
  *G01N 33/50* (2006.01)
  *G01N 21/51* (2006.01)
  *G01N 15/14* (2006.01)
  *G01N 15/10* (2006.01)
  *G01N 15/00* (2006.01)
  *G01N 21/47* (2006.01)
  *G01N 15/02* (2006.01)

(52) U.S. Cl.
  CPC ............... *G01N 2015/1497* (2013.01); *G01N 2021/4707* (2013.01); *G01N 2021/4711* (2013.01); *G01N 2021/4723* (2013.01)

(56) References Cited

OTHER PUBLICATIONS

Angular distribution of light scattered by single biological cells and oriented particle agglomerates, J. Neukammer et al. Applied Optics, vol. 42, No. 31, Nov. 1, 2003 (Year: 2003).*

Berne et al., "Dynamic Light Scattering: With Applications to Chemistry, Biology, and Physics", 2000, pp. iii-49, Dover Publications Inc.

United States Patent and Trademark Office, Office Action of U.S. Appl. No. 14/248,285, dated Sep. 28, 2015.

United States Patent and Trademark Office, Office Action of U.S. Appl. No. 14/248,285, dated Feb. 24, 2016.

* cited by examiner

EARLY WARNING OF CHANGES IN HEALTH AND ROBUSTNESS USING NARROWLY FORWARD SCATTERED LIGHT TO TRACK EASE OF MORPHOLOGICAL CHANGES OF BLOOD CELLS

CROSS REFERENCE TO RELATED APPLICATIONS

This application is a continuation-in-part of U.S. patent application Ser. No. 14/248,285, filed Apr. 8, 2014, which is incorporated herein by reference.

FIELD OF THE DISCLOSURE

The disclosure is generally directed at health monitoring, and more specifically, is directed at a system and method for early warning of changes in health and robustness using narrow forward scattered light to track ease of morphological changes of blood cells.

SUMMARY OF THE DISCLOSURE

The disclosure is directed at a method and apparatus for health monitoring. The disclosure provides a novel system and method for early warning of changes in health and robustness. The early warning system determinations can be obtained via a useful, reliable, and sensitive tracking of ease of morphological changes in blood cells using a tracking value (T) defined by a tracking equation: $T=\Sigma|Fi-Si|$. In the equation, Fi represents a first scattered light intensities in a first scattered light intensity angular distribution detected at angles I i and Si represents a second scattered light intensities in a second scattered light angular distribution detected at angles i. The summation is performed over angles i where i is between 0 and 4 degrees and, more preferably, between 0 and 2 degrees.

BRIEF DESCRIPTION OF THE DRAWINGS

Embodiments of the present disclosure will now be described, by way of example only, with reference to the attached Figures.

DETAILED DESCRIPTION

A system to track ease of morphological changes in blood cells comprises a sample container to contain a suspension of blood cells from a blood sample having a cells per volume sample concentration. Determination of forward scattering measurements from a cell suspension allows for assessing the effect of the challenge agent(s) on the blood sample as a whole to assess a response based on cells as an ensemble. Also, morphological changes can also be determined using simpler point-of-use devices.

The system also comprises an incident light source providing incident light. The incident light has an incident light central axis. The incident light central axis has a path length through blood samples in the sample container. Passage of the light through the sample container produces a forward scattered light angular range away from the incident light central axis.

The system also comprises a forward scattered light detector. The forward scattered light detector detects a scattered light intensity angular distribution. The scattered light intensity angular distribution comprises incident light scattered by a blood cell suspension in the sample container into the forward scattered light angular range. After detection, the system may include a processor for determining the light intensity angular distribution.

The system also comprises configuration together:
 of the incident light,
 of the forward scattered light detector,
 of the sample concentration, and
 of the incident light central axis path length through blood samples in the sample container, so that stochastic fluctuations of orientations of electric dipole moments of blood cells in an ensemble of blood cells along the incident light central axis path length through blood cell suspension in the sample container add incident light scattered by the ensemble of cells into the forward scattered light angular range away from the incident light central axis;

The basic science of light scattering by ensembles of scatterers, which is well known to persons having ordinary skill in this art, is detailed, for example, in the book: Bruce J. Berne, Robert Pecora, Dynamic Light Scattering: With Applications to Chemistry, Biology, and Physics, Wiley, 1976 and Courier Dover Publications, 2000.

It is a new result and an unexpected discovery that the incident light, the forward scattered light detector, the sample concentration, and the path length can be configured together to track of ease of morphological changes in blood cells shown in FIG. 1, FIG. 2, FIG. 3, FIG. 4, and FIG. 5.

It is a new result and an unexpected discovery that useful, reliable, and sensitive tracking of ease of morphological change in blood cells can be obtained from light scattered by the blood cells into a narrow forward angular range which includes at least a first blood cell scattering peak and a second blood cell scattering peak which can be seen below one degree in FIG. 1 and FIG. 2.

The location of these two scattering peaks depends on the wavelength of incident light.

Sensitive and reliable results are obtained using a 780 nm wavelength laser with power output of 5 mW, sample container with path lengths ranging from 2 mm to 10 mm in samples diluted to 5% blood and 95% physiological phosphate buffered saline (buffer), with longer path lengths requiring a greater amount of buffer. Other laser wavelengths, sample container path lengths, and buffers can also provide sensitive and reliable results.

The system also comprises a first test blood cell suspension obtained from the blood sample and a second test blood cell suspension obtained from the blood sample. Subsequent test blood cell suspensions can also be obtained from the blood sample.

The system also comprises a first scattered light intensity angular distribution detected by the forward scattered light detector. The first scattered light intensity angular distribution comprises incident light scattered by the first test blood sample in the sample container into the forward scattered light angular range.

For the detecting, accumulation of 100 to 500 exposures by a CMOS CCD sensor with 640×480 pixels per inch at a speed of 50 millisecond/exposure provides sensitive and reliable results. Other detectors and exposure accumulations can also give sensitive and reliable results.

The system also produces a second scattered light intensity angular distribution which can be detected by the forward scattered light detector. The second scattered light intensity angular distribution is determined by directing incident light at a second blood cell suspension from the sample, the light then being scattered by the second blood cell suspension in the sample container into the forward scattered light angular range. The second blood cell suspension may be seen as a challenge agent added to the blood cell suspension from the sample. In one embodiment, there is time interval before obtaining the first and second scattered light intensity angular distributions such that the challenge agent may be applied.

A challenge agent which can cause morphological change to blood cells can challenge the second test blood sample for the challenge time interval. If a chosen challenge agent does not cause morphological changes to the blood cells, diagnostic information of either the blood cells or the challenge agent can be inferred.

There are many ways the first test blood cell suspension and the second test blood cell suspension might be obtained. For example, the first test blood cell suspension and the second test blood cell suspension can be obtained from the same blood sample and the challenge agent added to the second test blood cell suspension. Then the first scattered light intensity angular distribution is obtained or determined from the first test blood cell suspension. After the challenge time interval the second scattered light intensity angular distribution can be obtained or determined from the second test blood cell suspension to which the challenge agent was added.

For example, the first test blood cell suspension can be obtained from the blood sample and the first scattered light intensity angular distribution obtained. Then, the challenge agent can be added to the first test blood cell suspension, and then after a challenge time interval, the second scattered light intensity angular distribution can be obtained from the blood cell suspension to which the challenge agent was added. This example assumes that there is no important change in the first test blood sample before the challenge agent is added.

In another embodiment, the first test blood cell suspension can be obtained from the blood sample and the first scattered light intensity angular distribution obtained. Later the second test blood cell suspension can be obtained from a second blood sample from the organism and the challenge agent added to the blood cell suspension from the second blood sample. After the challenge time interval, the second scattered light intensity angular distribution can be obtained. This example assumes that there is no important change to the blood between obtaining the first blood sample and the second blood sample.

For example, the challenge agent can be added to at least part of the blood sample and the first test blood cell suspension obtained from the blood sample and the first scattered light intensity angular distribution obtained. Then after the challenge time interval, the second scattered light intensity angular distribution obtained. This type of a measurement provides a kinetic measurement of the effect of the challenge agent over a time period and can be repeated if more kinetic data is desired.

For example, the second test blood sample can be obtained from an organism after the organism has undergone a treatment. In this example, the treatment can be seen as the challenge agent.

Figure 1:
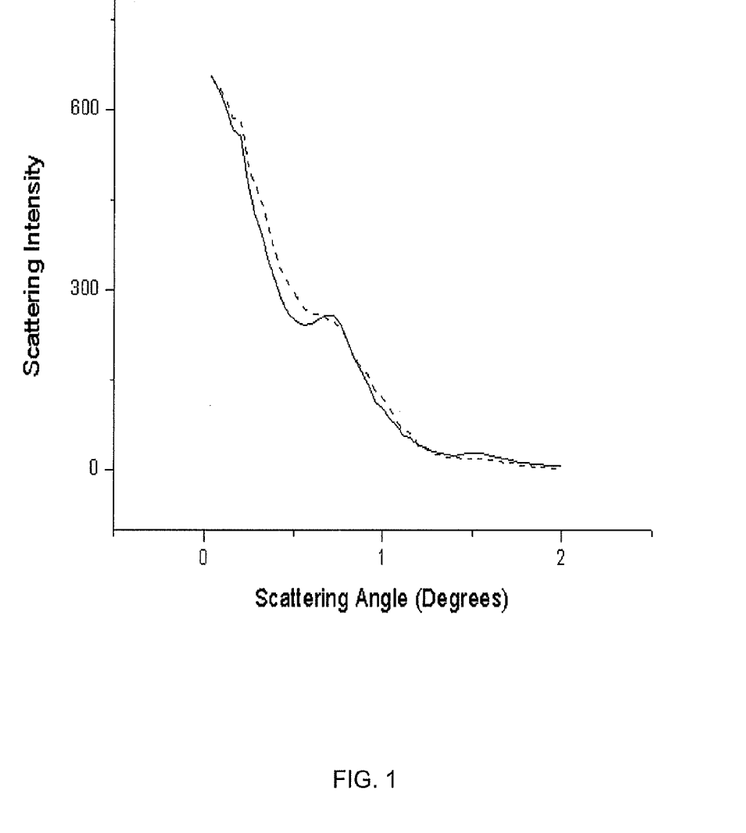
FIG. 1 shows scattered light intensity angular distributions:
 by a first test blood cell suspension obtained from a blood sample (solid curve), and
 by a second test blood suspension obtained from the same blood sample (dotted curve),
 with the second test blood suspension being challenged for a challenge time interval by a challenge agent which can cause morphological changes in the blood cell suspension.
Figure 2:
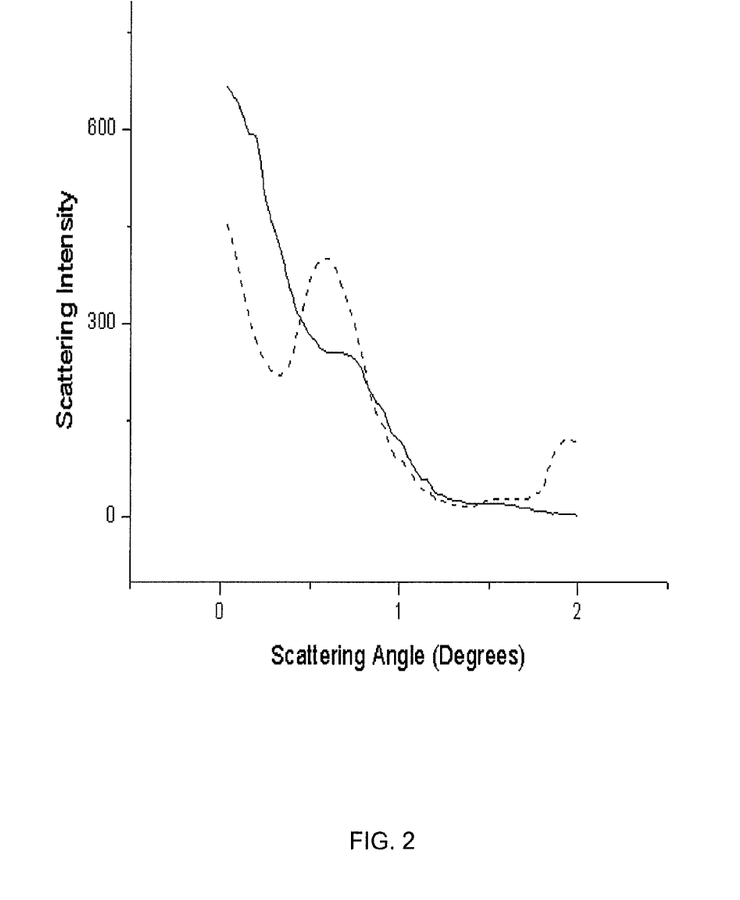
FIG. 2 shows scattered light intensity angular distributions:
 by a first test blood suspension from a second blood sample (solid curve) obtained from a different source, and
 by a second test blood suspension from the second blood sample (dotted curve),
 with the second test blood suspension being challenged for a challenge time interval by a challenge agent which can cause morphological changes in blood cells, and
 with the greater change between the solid and dotted curves here being because the challenge agent could more easily cause morphological changes in the blood sample used for FIG. 2 than in the blood sample used for FIG. 1.

FIG. 1 and FIG. 2 show first scattered light intensity angular distribution and a second scattered light intensity angular distribution. A challenge agent which can cause morphological change to blood cell suspension was added to the suspension after the first scattered light intensity angular distribution was obtained and a second scattered light intensity angular distribution was taken after a challenge time interval.

The difference occurs because the cells are morphologically changed by the challenge agent. Large scatterers, such as cells and cell nuclei for example, scatter into the narrowly forward angular range. Smaller scatterers such as other cell parts for example, scatter to larger forward angular range. Challenge agents can be selected to affect various cell parts. Conversely, it can be determined what parts of cells are being affected by challenge agents by changes in the angular range.

FIG. 1 is for "good nutritional status" because that is the self-report by the person providing this blood sample. FIG. 2 is for "poor nutritional status" because that is the self-report by the person providing this blood sample.

The difference between FIG. 1 and FIG. 2 shows that "poor nutritional status" makes it easier for a challenge agent to cause morphological change.

In FIG. 1, FIG. 2, FIG. 4, and FIG. 5 the numbers along the vertical axes are scattering intensities in arbitrary units. The numbers along the horizontal axes are angles away from the incident light central axis. Light very close to zero degrees is blocked to reduce or prevent the saturation of the detector by the laser.

Based on the first and second scattered light intensity angular distributions, a tracking value can be calculated which tracks change between the first scattered light intensity angular distribution and the second scattered light intensity angular distribution.

A tracking value (T) can be obtained using a tracking equation:

$$T = \Sigma |F_i - S_i|,$$

with $F_i$ comprising first scattered light intensities in the first scattered light intensity angular distribution detected at angles i, with $S_i$ comprising second scattered light intensities in the second scattered light angular distribution detected at angles i, and with the summation being over angles i.

There are many ways, including just visual inspection, that change between a first scattered light intensity angular distribution and a second scattered light intensity angular distribution might be tracked. It is a new result and unexpected discovery that the tracking equation above provides sensitive, reliable, and useful results.

Challenge agents are any agents which can cause morphological change to blood cells like that shown in FIG. 1 and FIG. 2. Challenge agents can be reactive oxygen species such as hydrogen peroxide. Challenge agents can be treatments such as the antivirals of FIG. 5. Challenge agents can be pathogens. Challenge agents can be chemicals such as antibiotics. Challenge agents can be electromagnetic radiation.

In FIG. 1, FIG. 2, FIG. 3, and FIG. 4 the challenge agent was hydrogen peroxide with a fifteen second challenge time interval.

Results equivalent to results seen in FIG. 1, FIG. 2, FIG. 3, and FIG. 4 can be obtained using ultraviolet light as the challenge agent. Using ultraviolet light has the advantage of being more easily standardized and does not involve a mechanical step of adding a challenge agent to a sample.

More than one means to challenge a sample can be used singly and alternatively together and alternatively serially. When no challenge agent is added and there is a challenge time interval between a first scattered light intensity angular distribution and a second scattered light intensity angular distribution, the tracking value will show change over time due to intrinsic challenge. This can be used to assess the suitability of the challenge time interval.

Figure 3:
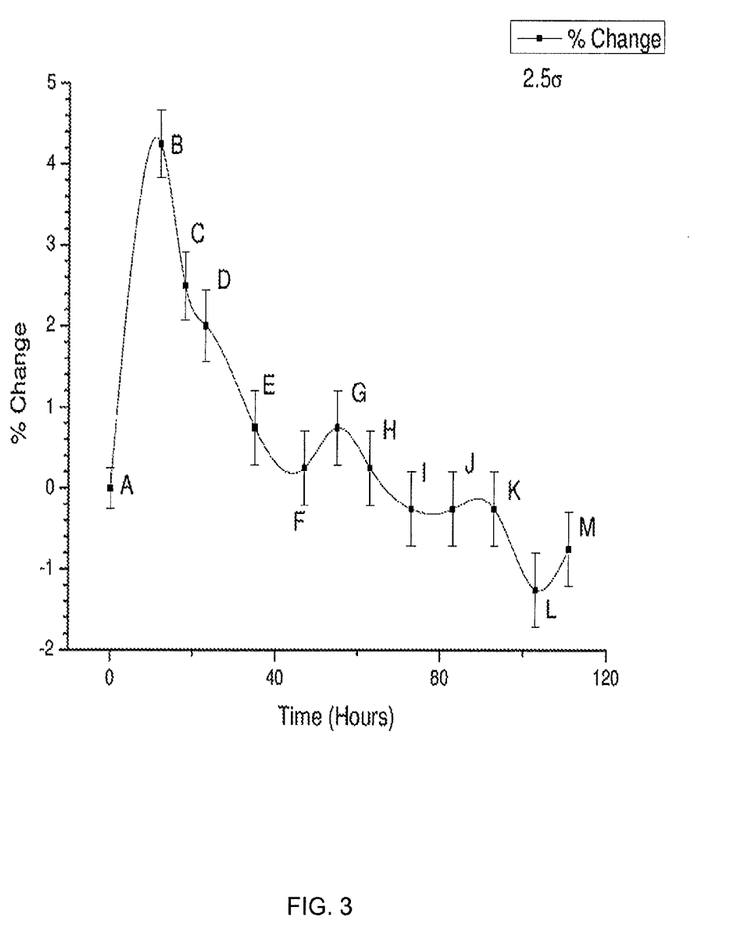
FIG. 3 is a compilation of measurements like those of FIG. 1 and FIG. 2 to show tracking of ease of morphological changes related to food eaten taken from the same person at time intervals shown on the x-axis.

Tracking over time of the ease of morphological change to blood cells in relation to food eaten is shown in FIG. 3. The vertical axis is percent change of the tracking value, all percent changes reckoned from the tracking value (T) at zero point—data point A—at zero hours. The horizontal axis is elapsed hours.

An increase occurs when the challenge agent more quickly causes morphological change to blood cells that result in an increase in the tracking value. A decrease occurs when the challenge agent less quickly causes morphological change to blood cells that result in a decrease in the tracking value.

Data points labeled A, B, C, D, E, F, G, H, I, J, K, L, and M correspond to tracking values obtained using the equation for tracking value from measurements like those shown in FIG. 1 and FIG. 2 made at each of the labeled data points.

This tracking example is related to changes in the tracking value resulting from the food eaten: About forty five minutes after data point A the person ate an 8 oz steak, fries, carrots, cheesecake, and wine. Just after data point B the person ate spinach salad with cheese vinegar/olive oil dressing and four oz. chicken. Shortly before data point D the person ate tomato soup, grilled salmon, spinach salad with vinegar/olive oil dressing, and almonds. Shortly before data point F the person ate oatmeal. Mid-way between data points H and I the person ate fish and vegetables. Shortly after data point J the person ate fish and vegetables.

Figure 4:
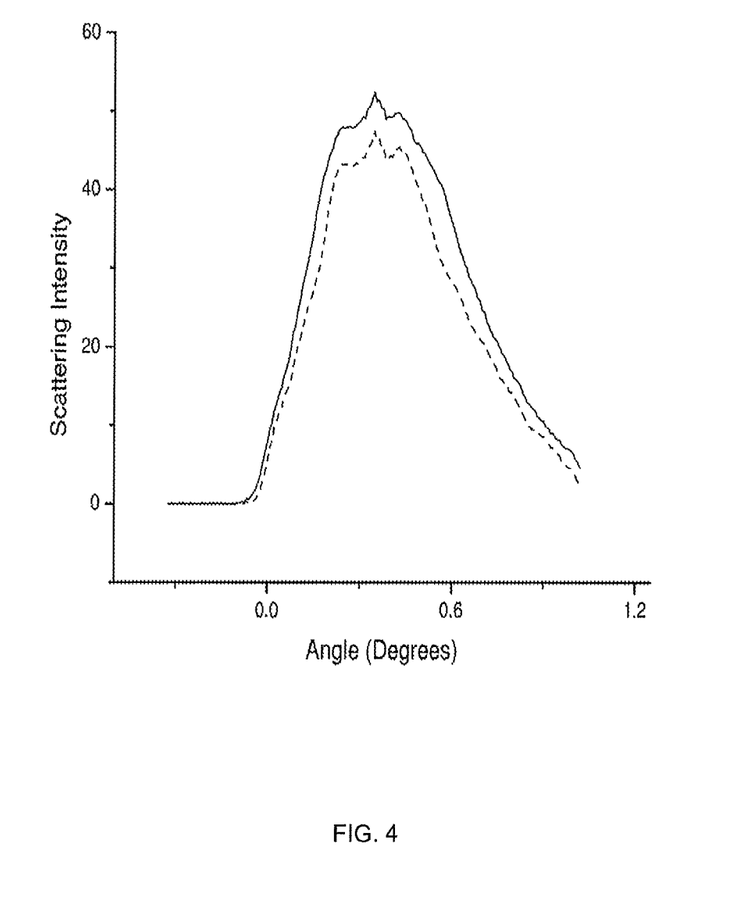
FIG. 4 shows scattered light intensity angular distributions:
 by a first test blood suspension from a blood sample (solid curve), and
 by a second test blood suspension from the same blood sample (dotted curve),
 with the second test blood suspension being challenged for a challenge time interval by a challenge agent which can cause morphological changes in blood cells,
 with the difference between the two angular distributions giving an early warning of developing pneumonia in a cow which had been constantly monitored and with no other sign of any developing problem.

FIG. 4 shows early warning of developing pneumonia in a cow. This cow had been constantly monitored by a thermometer in the fore-stomach. The thermometric tracking showed no sign of a developing problem. The system described and claimed here gave an early warning leading to early treatment so that full pneumonia did not develop and the cow recovered quickly.

Another cow was not expected to recover from *E. coli*. The system described and claimed here showed that the cow was getting close to normal after antibiotic treatment which turned out to be the case.

Early work with race horses indicates that increasing ease of morphological change of blood cells shown by the tracking value (T) gives early warning of decrease of robustness shown by decrease of performance in speed and endurance.

In an option, the system can also comprise a third test blood suspension obtained from the blood sample and a third scattered light intensity angular distribution detected by the forward scattered light detector obtained after the challenge time interval between the first scattered light intensity angular distribution and third scattered light intensity angular distribution. The third scattered light intensity comprising incident light scattered by the third test blood sample in the sample container into the forward scattered light angular range.

In this option a second challenge agent which can cause morphological change to blood cells can challenge, or change, the third test blood cell suspension for the challenge time interval.

In this option a second tracking value between the first scattered light intensity angular distribution and the third scattered light intensity angular distribution can be determined.

Figure 5:
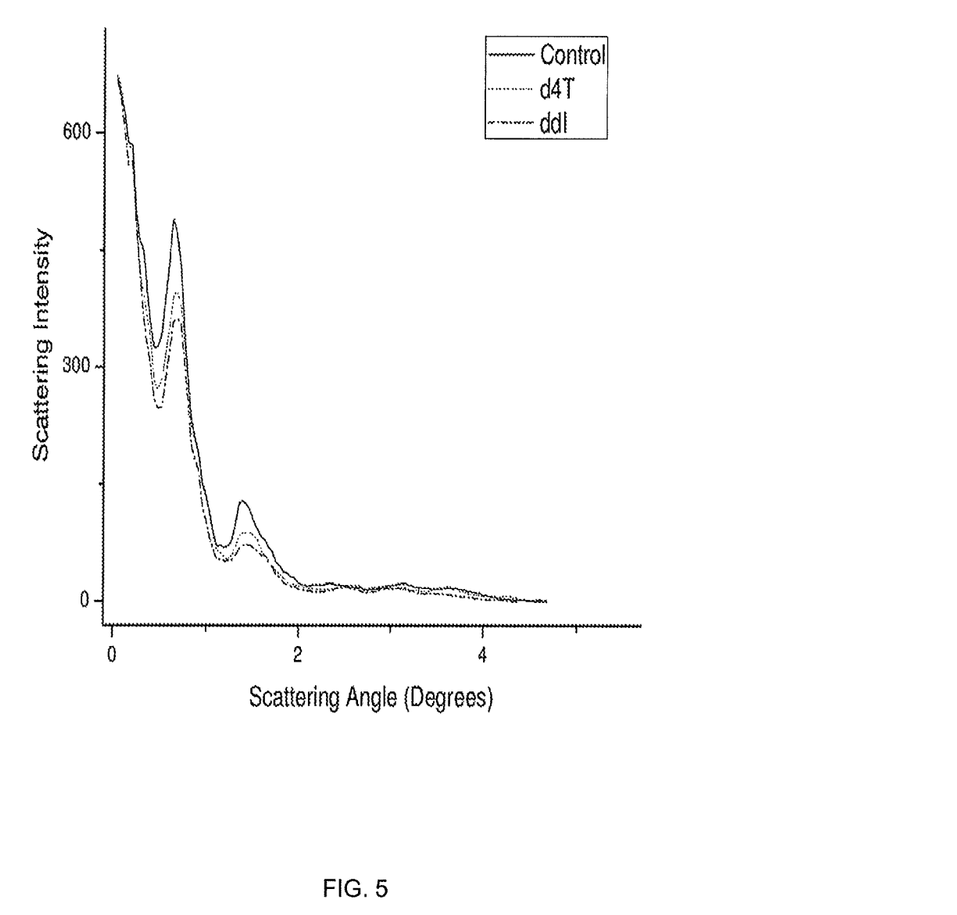
FIG. 5 shows scattered light intensity angular distributions
 by a first test blood suspension from a blood sample (solid curve) and
 by a second test blood suspension from the same blood sample (dotted curve) with a first antiviral added, and
 by a third test blood suspension (dashed curve) from the same blood sample with a second antiviral added,
 with the second antiviral more easily causing morphological changes.
Figure 6:
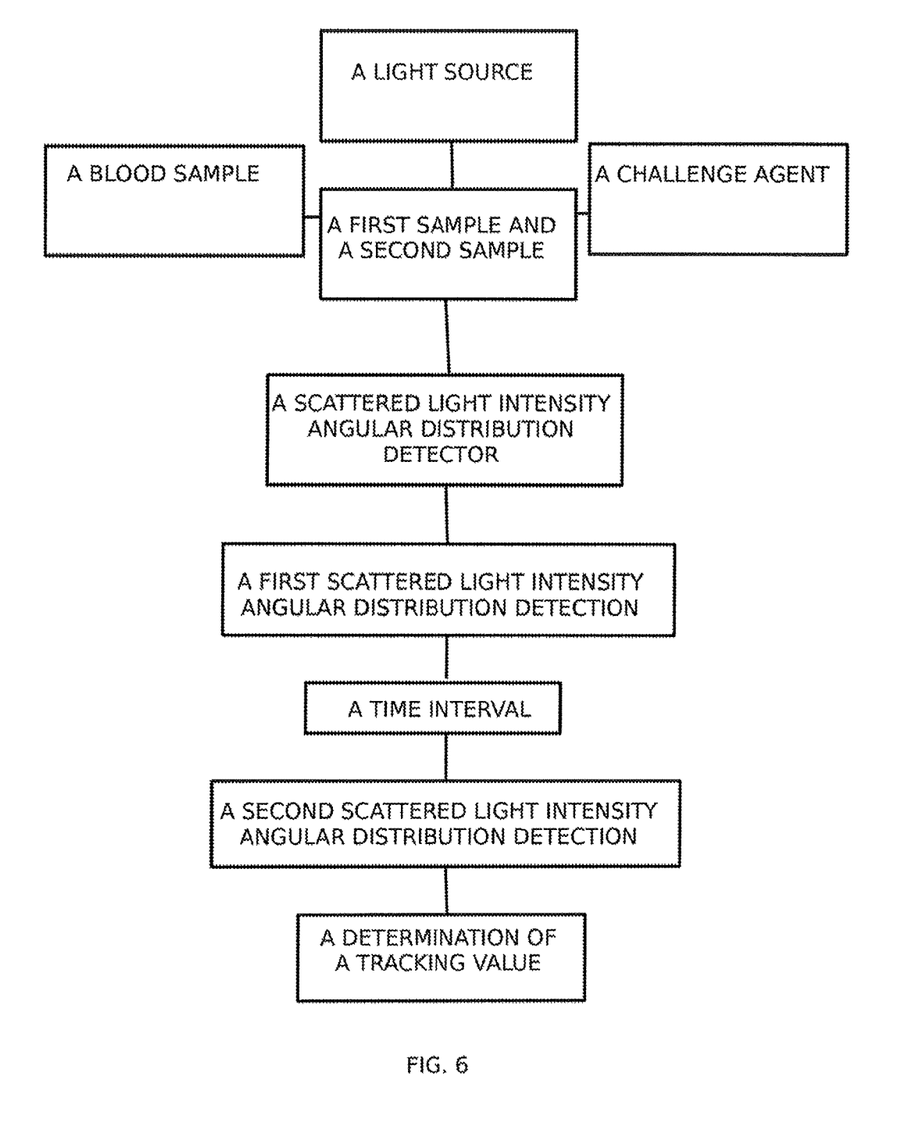
FIG. 6 is a schematic diagram of an apparatus for early warning of changes in health and robustness using narrowly forward scattered light to track ease of morphological changes of blood cells.

FIG. 5 shows a first scattered light intensity angular distribution (solid curve) scattered by a first test blood cell suspension obtained from a blood sample from a person infected with HIV/AIDS, a second scattered light intensity angular distribution (dotted curve) scattered by a second test blood cell suspension obtained from the same blood sample with a first antiviral efficacious for the HIV/AIDS infection of the person challenging the blood cell suspension for the challenge time interval, and a third scattered light intensity angular distribution (dashed curve) scattered by a blood cell suspension obtained from the same blood sample with the addition of a second antiviral equally efficacious for the HIV/AIDS infection of the person challenging the blood cell suspension for the challenge time interval.

Visual inspection of these three distributions shows that the second antiviral more easily causes morphological change to the person's blood, which is useful clinical information.

The new and unexpected result shown in FIG. 5 can also be obtained in comparison of treatments for various conditions.

FIG. 1, FIG. 2, FIG. 3, FIG. 4, and FIG. 5 show that the unexpected discoveries here provide new, reliable, sensitive, and useful tracking of ease of morphological changes in blood cells.

"Reliable" here means that the changes between first and second scattered light intensity angular distributions, depicted in FIG. 1 for example, are greater than random changes so that if the measurements, of FIG. 1 and FIG. 2 for example, were repeated many times, then the results would fall in a narrow confidence interval with high probability. For example, 4% of measurement repetitions for each of the measurements in FIG. 3 would fall within the error bars shown for each data point.

"Sensitive" here means that changes depicted in FIG. 1 and in FIG. 2, for example, track small percent changes as depicted in FIG. 3.

"Useful" here means that changes depicted in FIG. 1, FIG. 2, FIG. 3, FIG. 4, and FIG. 5 can be related to health and robustness. Greater ease of morphological change of blood cells by challenge agents can occur because of an otherwise pre-symptomatic infection, because of poor diet, because of effects of treatments, or because of various factors which make it easier for challenge agents to cause morphological changes in blood cells.

Blood samples can be whole blood and can be less than all the constituents of whole blood. For example, the blood cells used in the measurements shown in FIG. 5 had a portion of white blood cells removed.

Figure 7:
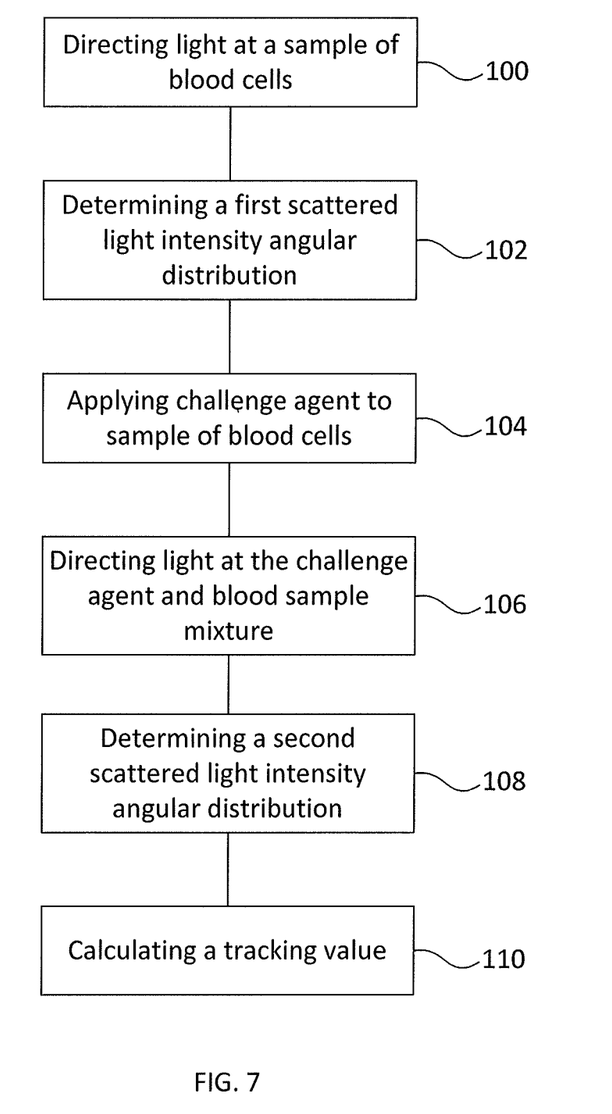
FIG. 7 is a flowchart outlining a method of tracking morphological change in blood cells.

Turning to FIG. 7, a flowchart outlining a method of tracking morphological changes in blood cells is shown. Initially, light is directed 100 an ensemble of suspended blood cells from a sample of blood. The light preferably includes an incident light central axis. A first scattered light intensity angular distribution is then determined 102. After determining the first angular distribution, a challenge agent is applied to the sample of suspended blood cells 104. The challenge agent preferably morphologically changes the blood cells within the sample of blood cells. The challenge agent may be applied after a predetermined time interval. The combination of the sample of blood cells and the challenge agent may be seen as a challenge agent and blood sample mixture.

In one embodiment, application of the challenge agent may be seen as applying a treatment to the blood sample. The challenge agent may be, but not limited to, a reactive oxygen species, an antiviral, a pathogen, an antibiotic or electromagnetic radiation.

The same light, or a different light, is then directed 106 at the blood cells suspended within the challenge agent and blood sample mixture. Either the previous light or a new light may be used with the requirement that the light includes an incident light central axis. A second scattered light intensity angular distribution is then determined 108. Based on the first and second scattered light intensity angular distribution values, a tracking value is then calculated or determined 110.

It will be understood that the calculation of the tracking value and the determinations of the various scattered light intensity angular distributions may be performed by the processor.

In another embodiment, first and second blood samples may be obtained from the sample of blood samples so that testing may be performed on independent samples.

In one embodiment, the tracking value may be calculated by the equation:

$$\Sigma_{i=0}^{i=4} |Fi - Si|,$$

such as disclosed above where i is between 0 and 4 degrees and more preferably between 0 and 2 degrees.

If necessary, the blood sample may be further manipulated (via the addition of a further challenge agent) to obtain or determine other scattered light intensity angular distribution values in order to calculate other tracking values.

In the preceding description, for purposes of explanation, numerous details are set forth in order to provide a thorough understanding of the embodiments. However, it will be apparent to one skilled in the art that these specific details may not be required. In other instances, well-known structures may be shown in block diagram form in order not to obscure the understanding. For example, specific details are not provided as to whether elements of the embodiments described herein are implemented as a software routine, hardware circuit, firmware, or a combination thereof.

Embodiments of the disclosure or components thereof can be provided as or represented as a computer program product stored in a machine-readable medium (also referred to as a computer-readable medium, a processor-readable medium, or a computer usable medium having a computer-readable program code embodied therein). The machine-readable medium can be any suitable tangible, non-transitory medium, including magnetic, optical, or electrical storage medium including a diskette, compact disk read only memory (CD-ROM), memory device (volatile or non-volatile), or similar storage mechanism. The machine-readable medium can contain various sets of instructions, code sequences, configuration information, or other data, which, when executed, cause a processor or controller to perform steps in a method according to an embodiment of the disclosure. Those of ordinary skill in the art will appreciate that other instructions and operations necessary to implement the described implementations can also be stored on the machine-readable medium. The instructions stored on the machine-readable medium can be executed by a processor, controller or other suitable processing device, and can interface with circuitry to perform the described tasks.

The above-described embodiments are intended to be examples only. Alterations, modifications and variations can be effected to the particular embodiments by those of skill in the art without departing from the scope, which is defined solely by the claims appended hereto.

What is claimed is:

1. A method of generating a tracking value to assist in determining morphological changes in a suspension of blood cells, the method comprising:
   obtaining the suspension of blood cells from a blood sample, the suspension of blood cells having a cells per volume concentration;
   directing light having an incident light central axis at a group of blood cells within the suspension of blood cells;
   determining a first scattered light intensity angular distribution;
   applying a challenge agent to the suspension of blood cells to morphologically change blood cells in the suspension of blood cells, wherein application of the challenge agent produces a challenge agent and blood suspension mixture;

directing light having the incident light central axis at a suspended group of blood cells within the challenge agent and blood suspension mixture;

determining a second scattered light intensity angular distribution; and calculating a tracking value based on the first scattered light intensity angular distribution and the second scattered light intensity angular distribution;

wherein the tracking value is obtained by the equation $T=\Sigma_{i=0}^{i=4}|Fi-Si|$, with Fi representing first scattered light intensities in the first scattered light intensity angular distribution detected at angles i where i represents a forward scattered light angular range, with Si representing second scattered light intensities in the second scattered light angular distribution detected at angles i where i represents the forward scattered light angular range, and with the summation being over angles i where i is between 0 and 4 degrees.

2. The method of claim 1 further comprising, before directing light at the suspended group of blood cells, obtaining a first blood cell suspension from the blood cell sample.

3. The method of claim 2 further comprising, before applying the challenge agent, obtaining a second blood cell suspension from the blood cell sample, the second blood cell suspension being the sample of blood cells to which the challenge agent is applied.

4. The method of claim 3 further comprising:

obtaining an additional blood cell suspension from the blood cell sample;

applying another challenge agent to the additional blood cell suspension, the another challenge agent being the same or different from the challenge agent applied to the second blood cell suspension;

directing light having the incident light central axis at the blood cell suspension;

determining a third scattered light angular distribution; and calculating a second tracking value based on the first scattered light intensity angular distribution and the third scattered light intensity angular distribution.

5. The method of claim 1 wherein applying the challenge agent occurs after a predetermined challenge time period.

6. The method of claim 1 wherein applying the challenge agent comprises:

applying a treatment to the blood cell sample.

7. The method of claim 1 wherein the challenge agent is a reactive oxygen species, an antiviral, a pathogen, an antibiotic, ultraviolet light or electromagnetic radiation.

8. The method of claim 1 wherein the angle i is between 0 and 2 degrees.

* * * * *